United States Patent [19]

Revel et al.

[11] Patent Number: 4,808,523

[45] Date of Patent: Feb. 28, 1989

[54] CONSTITUTIVE PRODUCTION OF HUMAN IFN-β1 BY MAMMALIAN CELLS TRANSFORMED BY THE IFN-β1 GENE FUSED TO AN SV40 EARLY PROMOTER

[75] Inventors: Michel Revel, Rehovot; Menachem Rubinstein, Givat Shmuel, both of Israel

[73] Assignee: Yeda Research and Development Co., Ltd., Rehovot, Israel

[21] Appl. No.: 669,259

[22] Filed: Nov. 7, 1984

[51] Int. Cl.$^4$ .................... C12P 21/00; C12N 15/00; C12N 5/00

[52] U.S. Cl. .................................. 435/68; 435/240.2; 435/240.25; 435/320; 435/811; 424/85.6

[58] Field of Search .................. 435/68, 240, 172.2, 435/320, 240.2, 240.25; 424/85; 530/351

[56] References Cited

U.S. PATENT DOCUMENTS 4,485,017  11/1984  Tan et al. .......................... 435/811

OTHER PUBLICATIONS

Fiers et al., Phil. Trans. R. Soc., Ford B299, pp. 29–38, 1982.
Chemical Abstracts, vol. 98, Abstract No. 1171a, 1983.
Chemical Abstracts, vol. 98, Abstract No. 120598w, 1983.
McCormick et al., Molecular and Cellular Biology, vol. 4, pp. 166–172, 1984.
Knight, Jr., Methods in Enzymology, vol. 78, pp. 417–421.

*Primary Examiner*—Blondel Hazel
*Attorney, Agent, or Firm*—John P. White

[57] ABSTRACT

The invention concerns the production of the human fibroblast interferon, IFN-β1 by cells of mammalian origin which are capable of constitutively expressing a DNA sequence encoding for IFN-β1, producing the IFN and secreting it into the surrounding culture media.

A specific embodiment of the invention comprises a methotrexate resistant chinese hamster ovary cell containing one or more pSVEIF molecules. The pSVEIF molecule contains a DNA sequence encoding for human INF-β1 fused about 60 base pairs downstream from SV40 early start gene. The cell is capable of constitutively expressing the sequence encoding IFN-β1, producing IFN-β1 glycoprotein and secreting it into the surrounding medium.

The invention also concerns methods of producing IFN-β by culturing and growing the cells of the invention, and isolating and purifying the IFN-β1 product.

11 Claims, 4 Drawing Sheets

Figure 2.

```
              -110           -100            -90            -80            -70            -60
svβ1(172bp)TAGTCCCGCCCCTAACTCCGCCCATCCCGCCCCTAACTCCGCCCAGTT CCGCCCATTCTC
β-1         TAGAAACTACTAAAATGTAAATGACATAGGAAAACTGAAAGGGAGAAGTGAAA GTGGGAAATTCC
α-C         TTTTTAAACACATGAAGAGAGTAAAGAG GAAACAAAAACACAGATAGAAA GTAAACTAGGGCAT
α-A         GCTGAAAACCCATGTAAAGAGTGTATAAA GAAAGCAAAAGAAGAAGTAGAAA GTAACACAGGGCAT
α-D         GCTCTAAACTCATGTAAAGAGTGCATGAAGGAAAGCAAAAGCAAAACAGAAAATGGAA GTGGCCAGAAGCAT
β-2         TCAGCCCCACCCCTCTCGCCCCACCCTCACCCTCAACAAGATTTATCAAATGTGGGATTTTCCCATGAG

-50            -40               ****              -20          -10         -1
svβ1        CGCCCCAT GGCTG  ACTAATTTTTTTTATTTATG   CAGAGGCCGAGGCCGCTCCGC CTCTGAGCTAT
β-1         TCTGAATA GAGAG  AGGACCATCTCATATAAATA   GCCCATACCCATGCAGAGAAGA CATTCTAACTG
α-C         TTAGAAAATGGAAATTAGTATGTTCAC TATTTA A   GA CCTATGCACAGAGCAAAG TCTTCAGAAAA
α-A         TTGAAAAATGTAAACGAGTAGTGTTCCC TATTTA A   GG C TAGGCACAAAGCAAG  TCTTCAGAGAA
α-D         TAAGAAAGTGGAAATCAGTATGTTCCC  TATTTA A   GG CATTTGCAGGAAGCAAGG  CCTTTCAGAGAA
β-2         TCTCAATATTAGAGTCTCAACC  CCCA ATAAATATAGGAC TGGAGATGTCT GAGGCTCATTCTGC 20             30             40             50             60
svβ1        TCCAGAACTAGTGAGGAGGCTTTTTGGAGGCCTAGGCCTTTTGCAAAAGCTT-------AACATG
β-1         CAACCTTTCGAAGCCTTTGCTCTGGCACAACAGGTAGTAGGCCACACTGTTCGTGTTGTCAACATG
α-C         CCTAGAGACCCAAGTTCAAGGTTATCCATCTCAAGTAGCCTAGCAATATTGCAACATCC CAATG
α-A         CCTGGAGCCTAAGGTTAGGCTCAAGTCAACCAGTCAAGCATCTGCAACATCTACAATG
α-D         CCTAGAGCCCAAGGTTCAGATGCAGTCACCCATCTCAGCAAGCCCAGAAGTATCTGCAATATCTACGATG
β-2         CCTCGAGCCCACCGGGACGAAAGAGAAGCTCTATCTCCCCTCCAGGACCTATGAACTCCTTCTCCACAAG
              +
```

CONSTITUTIVE PRODUCTION OF HUMAN IFN-β1 BY MAMMALIAN CELLS TRANSFORMED BY THE IFN-β1 GENE FUSED TO AN SV40 EARLY PROMOTER

BACKGROUND OF THE INVENTION

Throughout this application various publications are referenced by the names of the authors and the year of publication within parentheses. Full citations for these references may be found at the end of the specification immediately proceding the claims. The disclosures of these publications in their entireties are hereby incorporated by reference into this application in order to more fully describe the state of art as known to those skilled therein as of the date of the invention described and claimed herein.

The major species of human fibroblast interferon (IFN-β) is coded for by a single gene IFN-β1 (Ohno and Taniguchi, 1981; Degrave et al, 1981; Lawn et al, 1981, Gross et al, 1981; Mory et al, 1981). Expression of this gene is activated in human fibroblasts which are virus-infected or have been induced by double-stranded (ds) RNA (Burke, 1980; Raj and Pitha, 1981). After poly (rI)(rC)-induction, mRNA accumulates transiently for 2-4 hours and there is only a limited excretion of IFN unless the cells are superinduced by addition of cycloheximide or other metabolic inhibitors, which leads to a more prolonged accumulation of mRNA (Tand and Armstrong, 1970; Cavalieri et al, 1977; Sehgal et al, 1978; Raj and Pitha, 1981, 1983). In superinduced human fibroblasts, the titers of IFN-β produced can reach 20-30,000 units/ml after 24 hours (Havell and Vilcek, 1972). Inducibility is a property of the human IFN-β1 gene promoter, and is conserved if the gene is transferred to foreign cells by stable cotransformation (Hauser et al, 1982; Ohno and Taniguchi, 1982; Canaani and Berg, 1982) or as part of a replicating viral vector such as BPV (Zinn et al, 1982; Mitrani-Rosenbaum et al, 1983) or SV40 (Maroteaux et al, 1983a; Tavernier et al, 1983). To eliminate the need for induction and achieve a more efficient IFN production, we have prepared a cell line in which the IFN-β1 gene is constitutively expressed and present in multiple copies.

The coding region of the IFN-β1 gene was fused to give the SV40 early gene promoter, and then transfected into chinese hamster ovary cells deficient in dihydrofolate reductase (Urlaub and Chasin, 1980) together with a selectable DHFR gene (Kaufman and Sharp, 1982). Amplification of the fused SV40-IFN-β1 DNA co-transfected with the DHFR gene, was obtained by selection of CHO transformants for resistance to increasing amounts of methotrexate (Alt et al, 1978; Ringold et al, 1981; Kaufman and Sharp, 1982). CHO cell lines excreting 200-300,000 units IFN-β per ml culture in 24 hours, i.e. 10 times more than human cells and without need for induction, were obtained. The human IFN-β1 produced by these hamster cells, has been purified by affinity chromatography on columns of monoclonal antibodies to native human IFN-β (Novick et al, 1983) and found to have the same physical properties and specific antiviral activity as the human product.

SUMMARY OF THE INVENTION

A cell of mammalian origin in which a DNA sequence encoding for the human fibroblast interferon IFN-β1 is constitutively expressed has been invented. In preferred embodiments of the invention this cell has been transformed with a plasmid comprising the DNA sequence encoding for IFN-β1 fused to the SV40 early promoter. The sequence encoding for IFN-β1 can be present in the cell in multiple copies.

In a preferred embodiment of the invention the cell is a chinese hamster ovary (CHO) cell which is resistant to methotrexate. The CHO cell is transformed with the plasmid pSVEIF which is a plasmid containing a DNA sequence encoding for human fibroblast interferon IFN-β1 fused about 60 base pairs downstream from the SV40 early start gene. This pSVEIF-CHO cell is capable of constitutively expressing the sequence encoding IFN-β1, producing the IFN-β glycoprotein and secreting it into the surrounding medium.

The invention also concerns clones of the cells produced in accordance with the methods of the invention and cell lines produced from these cells. The cell line CHO-β1-5-9, Pasteur Collection No. I-340 is a preferred embodiment of the invention. Another aspect of the invention is the production of human IFN-β with mammalian cells which are capable of constitutively expressing the sequence the glycoprotein product into the surrounding medium. The cells are grown in a suitable culture medium and on a suitable surface and maintained at a temperature of about 37° C. The culture medium is periodically changed. The medium that has been replaced is collected and contacted with an affinity chromatography adsorbent so as to retain the IFN-β1 secreted by the cells into the culture medium. The adsorbent containing the IFN-β1 is then washed with a suitable solution to remove the proteins other than the IFN-β1 which have not been adsorbed. After washing the adsorbent the IFN-β1 is eluted with a suitable solution. The eluate protein solution containing the IFN-β1 is purified by affinity chromatography with monoclonal antibodies prepared against IFN-β1 from human fibroblasts. The IFN-β1 bound to the monoclonal antibodies is eluted by washing with a suitable solution.

The invention also concerns human fibroblast interferon IFN-β glycoprotein produced by the methods of this invention.

BRIEF DESCRIPTION OF THE DRAWINGS

FIG. 2: Nucleotide sequence of the promoter region of various human IFN genes.

Figure 1:
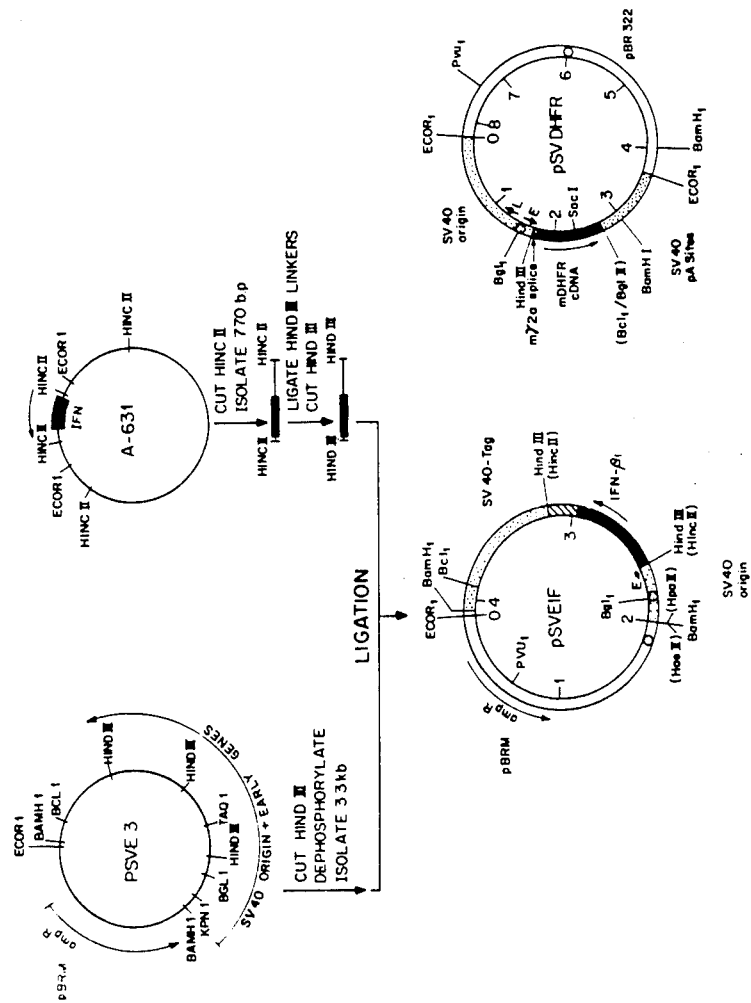
FIG. 1: Construction of the SV40 early promoter—IFN fusion, and map of the pSVDHFR plasmid containing the selectable dihyfrofolate reductase gene.

SVβ1 designates the SV40 early promoter which was fused (dotted line) to the coding region of IFNβ1 to form the pSVEIF-DNA of FIG. 1. β1 is the IFN-β1 promoter region (Ohno and Taniguchi, 1981). Three human IFN-α promoter regions (αC, αA and αD) are shown for comparison (Lawn et al., 1981b); IFN-αC was determined in our laboratory by L. Maroteaux. β2 designates another poly (rI)(rC)-inducible gene whose promoter sequence (Maroteaux et al, 1983a) was fused at the XhoI site (CTCGAG, shown by +) to the TaqI site (TCGA) of IFN-β1 at position +20 to produce pβ2pro-β1. Stars indicate TATA boxes, (72 bp) is the SV40 enhancer. Numbers are from the RNA start sites. Spaces were added to stress homologies.

Figure 3:
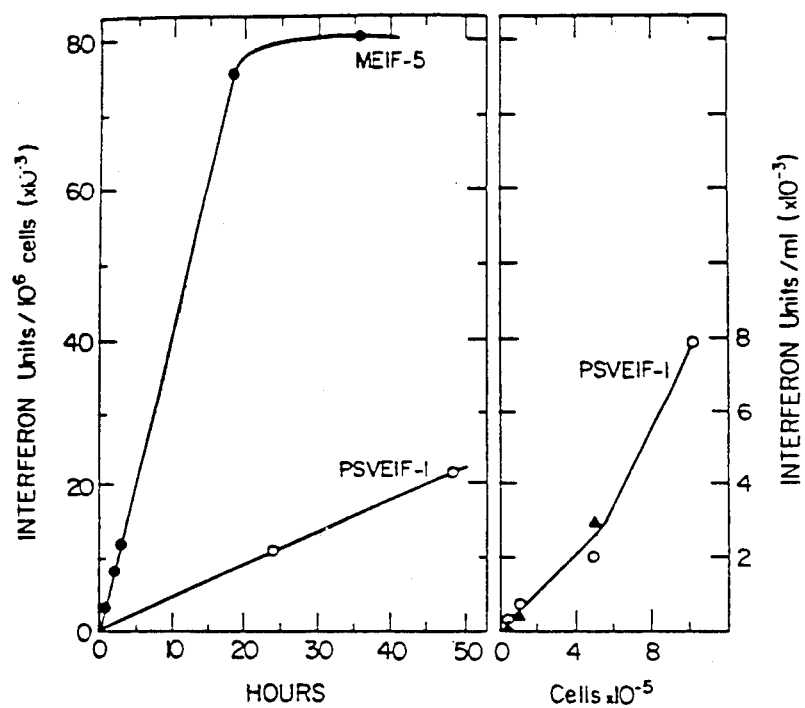

FIG. 3: Constitutive production of human IFN-β1 by transformed CHO clones. Left panel: IFN accumulated in the medium of pSVEIF and MEIF cells, at indicated time after changing the medium of 3 days-old semi-confluent cultures. Right panel: Cells were seeded at indicated density in 7 cm2 plates. Medium was changed after 1 day and IFN activity was determined 24 hours later (O, pSVEIF-1 CHO cells;/pSVEIF-2 CHO cells) (MEIF-5 cells are cells from the cell line CHO-$\beta_1$-S-9, Pasteur Collection No. I-340.).

Figure 4:
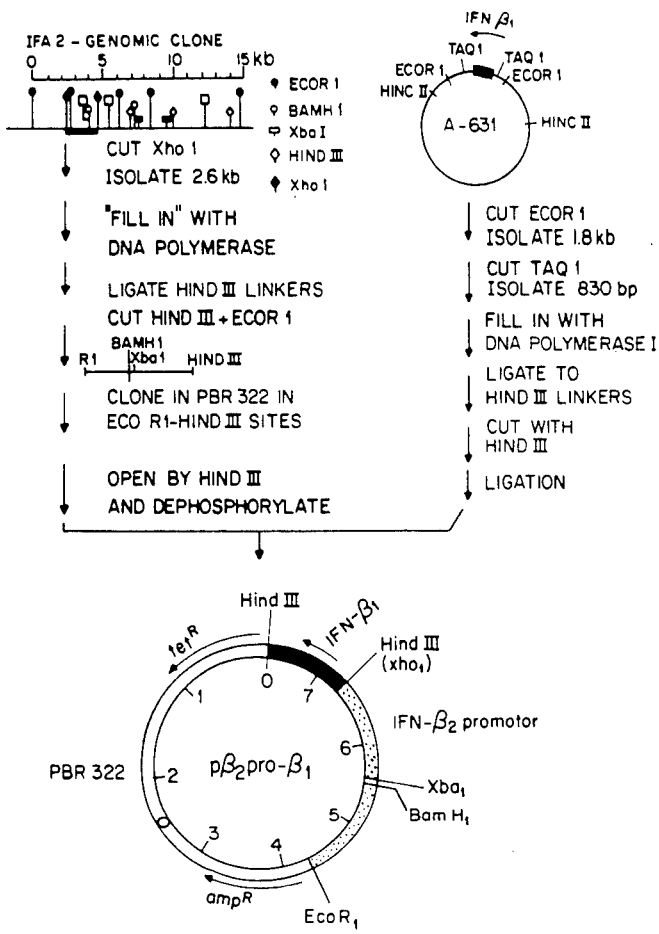

FIG. 4; Construction of p$\beta$2pro-$\beta$1 DNA.

DETAILED DESCRIPTION OF THE INVENTION

A cell of mammalian origin in which a DNA sequence encoding for the human fibroblast interferon IFN-$\beta$1 is constitutively expressed has been invented. A mammalian cell is transformed by methods known to those of ordinary skill in the art with a plasmid comprising the DNA sequence encoding for IFN-$\beta$1 fused to the SV40 early promoter. Transformed cells in which the sequence encoding for the IFN-$\beta$1 is present in multiple copies can be selected. These transformed mammalian cells capable of constitutively expressing the DNA sequence encoding for IFN-$\beta$1 are also capable of producing this glycoprotein and secreting it into the surrounding culture medium.

In a specific embodiment of the invention the sequence encoding for IFN$\beta$1 is fused at a position about 60 base pairs downstream from the early mRNA start. The sequence encoding for IFN-$\beta$1 is derived from the 1.83 kb Eco R1 fragment of human genomic DNA containing the IFN-$\beta$1 gene. A recombinant plasmid with these characteristics has been constructed and designated pSVEIF.

The mammalian cell is preferably a chinese hamster ovary cell, however, it can be any other mamalian cell such as a monkey or a mouse cell. A chinese hamster ovary cell that lacks dihydrofolate reductase activity can be used e.g. an CHO-KI-DHFR cell. If such a cell is used it can be transformed with pSVEIF and the selectable marker pSVDHFR. The pSVDHFR plasmid contains the dihydrofolate reductase gene and thus indicates if a successful transformation of the dihydrofolate reductase negative cells have occurred. The transformed cells can also be methotrexate resistant. Clones of pSVEIF-CHO cells were selected for resistance to methotrexate. These methotrexate resistant CHO cells showed a 10 to 20 fold increase in their constitutive production of IFN-$\beta$1 activity. These cells have been designated as MEIF-CHO cells.

The invention also concerns clones of the transformed mammalian cells and cell lines derived from these cells. In the preferred embodiment of the invention a cell line has been developed whose cells are capable of producing constitutively up to about 350,000 units IFN-$\beta$ per ml, by $10^6$ cells in 24 hours. This cell line has been designated CHO-$\beta_1$-5-9 and has been deposited with the Institut Pasteur Collection Nationale de Cultures de Microorganismes, Rue du Docteur Roux, 75724 Paris, France under accession number I-340.

The CHO-$\beta_1$-5-9 cell is a methotrexate resistant chinese hamster ovary cell which contains one or more pSVEIF molecules integrated in its genome. This pSVEIF plasmid as described above contains a DNA sequence encoding for the human fibroblast interferon IFN-$\beta$1 fused about 60 base pairs downstream from the SV40 early start gene. The MEIF-5-CHO cell can constitutively express the sequence encoding IFN-$\beta$1, produce the IFN-$\beta$ glycoprotein and secrete it into the surrounding medium.

The invention also concerns a method of producing human IFN-$\beta$1 with the cells of this invention, or by use of clones of these cells or cell lines derived from the mamalian cells of this invention e.g. CHO-$\beta_1$-5-9, Pasteur Institute I-340. The method comprises first growing the cells in a suitable culture medium e.g. Dulbecco's modified minimum essential medium with about 150 $\mu$g/ml 2-proline. The medium should contain a minimal amount of foreign protein, perferably about 1% fetal calf serum. The cells must also be grown on a suitable surface such as glass, plastic or other polymeric substances. The suitable surface may be in any practical form suitable for cell culture such as roller bottles, or microcarrier beads in a fermentor. The culture medium is maintained at 37° C. with periodical change of medium. The periodical change is perferably about every 24 hours, however, longer and shorter replacement periods may also be used. In the alternative the culture can be set up so that the medium is changed by a continuous flow process. By culturing the cells with this periodical change of culture medium, IFN-$\beta$ producing cell cultures have been maintained for a period of about 4 months.

The medium that has been replaced is collected and IFN-1 that has been secreted by the cells into the medium is isolated and purified. The medium can be stored at 4° C. The medium is contacted with an affinity chromatography adsorbent so as to retain the IFN-$\beta$1 secreted into the medium. Any suitable adsorbent can be used such as Blue Sepharose (Pharmacia). For example, Blue Sepharose was added to the medium and the resulting mixture was stirred for 16 hrs. The adsorbent containing the IFN-$\beta$1 is then washed with a suitable solution so as to remove the proteins other than IFN-$\beta$1 that have not been adsorbed. In the previous example, Blue Sepharose beads were collected by filtration and washed with 1.5 m KCl.

After washing the adsorbent the IFN-$\beta$1 is eluted from the adsorbent with a suitable solution. A 40% propylene glycol solution was used to elute the IFN-$\beta$1 from the Blue Sepharose. The eluate containing the IFN-$\beta$1 is then purified by affinity chromatography with monoclonal antibodies prepared against the IFN-$\beta$1 from human fibroblasts. The chromatography is preferably carried out on a column prepared by binding 7 mgs. IgG 117-1 per ml. of agarosepolyacryl hydrazide. The IFN-$\beta$1 is eluted from the monoclonal antibody column with a suitable solution capable of permitting the recovery of IFN-$\beta$1 such as 50 mM citric acid-HCl pH 2.

In a preferred embodiment of the invention the eluate containing the IFN-$\beta$1 is concentrated before purifying by affinity chromotography with monoclonal antibodies. The concentration can be done by any method suitable for the concentration of a protein solution known to those of ordinary skill in the art such as ultrafiltration under mild pressure.

The invention also concerns human fibroblast interferon IFN-$\beta$1 produced by the cells and methods of this invention.

The IFN-$\beta$1 produced by this invention can be dialyzed against acetate buffer of a pH of about 3.5 and supplemented with a composition comprising human serum albumin, fraction V, mannitol, and polyvinyl pyrrolidone (1000 to 50,000 Mr) per 0.1 to $10 \times 10^6$ units of IFN-$\beta$1. In a preferred embodiment of the invention the composition comprises about 40 mgs human serum albumin fraction V, about 10 mgs mannitol, about 40 mgs polyvinyl pyrrolidone (1000 to 50,000 Mr) per 0.1 to $10 \times 10^6$ units of IFN-$\beta$1. This composition improves the stability and shelf life of the IFN-$\beta$1.

RESULTS

Constitutive Production of IFN-$\beta$ in CHO Cells Transformed by the Human IFN-$\beta$1 Gene Fused to the SV40 Early Promoter A 1.83 kb EcoR1 fragment of human genomic DNA containing the IFN-$\beta$1, gene (Mory et al, 1981), subcloned in pBR322 (A631, FIG. 1), was digested with HincII. This enzyme cuts the IFN-$\beta$1 gene at 3 bp before the initiator ATG codon and at the poly (A) addition site (Ohno and Tanguchi, 1981). The HincII fragment was introduced by HindIII linkers into plasmid pSVE3 (Hartman et al, 1982) (FIG. 1) fusing the IFN-$\beta$1 coding region at 60 bp downstream from the SV40 early mRNA start; the resulting plasmid was designated pSVEIF (FIG. 1). Chinese hamster ovary cells CHO-K1 DHFR-, lacking dihydrofolate reductase activity (Urlaunb and Chasin, 1980) was transformed by the calcium phosphate coprecipitation technique (Graham and Van der Eb, 1973; Busslinger et al, 1981) with a 5:1 mixture of uncut pSVEIF-DNA and pSVDHFR-DNA (FIG. 1), the latter being the selectable marker. Transformants able to grow in medium lacking thymidine (DMEM with extensively dialized serum), were obtained at an efficiency of $10^{-4}$.

Culture supernatants of individual transformant clones (0.5–1×10^6 cells per ml) were screened for human IFN activity by measuring the reduction of VSV cytopathic effect on human FS11 diploid fibroblasts, in comparison to international IFN-$\beta$1 standards. Most of the pSVEIF-CHO clones tested, produced 5–10,000 units IFN per ml and 10^6 cells in 24 hours (Table 1). IFN accumulation in the culture medium was proportional to the number of cells seeded and to the time in culture (FIG. 3), as expected for constitutive expression. CHO cells transformed by pSVEIF-DNA, in which the IFN gene is oriented opposite to the SV40 promoter, did not produce IFN activity (Table 1).

TABLE 1

CONSTITUTIVE PRODUCTION OF HUMAN IFN-$\beta$1 IN CHINESE HAMSTER OVARY CELLS

| CHO cell clone | IFN-$\beta$1 produced Units/ml/10^6 cells/24 h | EcoR1 DNA fragments in Southern blots (kb) |
|---|---|---|
| pSVEIF | | |
| 1 | 10,000 | 4.2 + 4.8 + 2.3 |
| 2 | 10,000 | 4.2 + 3.7 |
| 5 | 6,000 | 4.2 + 2 |
| 7 | 12,000 | |
| 8 | 8,000 | 4.2 |
| 13 | 1,500 | |
| pSVEIF' (opposite orientation) | <4 | |
| MEIF (50 nM Methotrexate) | | |
| 5-1 | 200,000 | 4.2 + 2 |
| 5-3 | 128,000 | |
| 5.4 | 50,000 | |
| 7-8 | 2,000 | |
| 7-10 | 10,000 | |
| MEIF (1 μM Methotrexate) | | |
| 5-3* | 350,000 | |

Cells in 3 cm plates and 1 ml medium. IFN activity measured 24 hours after medium change and expressed per million cells. pSVEIF clones were obtained by co-transformation of CHO DHFR- cells with pSVEIF and pSVDHFR DNA (see FIG. 1). MEIF clones were derived from pSVEIF clones by selection with Methotrexate.

Hybridization of IFN-$\beta$1 DNA to Southern blots of total DNA from various pSVEIF-CHO clones showed that among the fragments released by EcoR1 digestion, one was always 4.2 kb (Table 1) while with BamH1, one was 2 kb. Thus, both EcoR1 and BamH1 release from the DNA of the transformed cells, IFN-$\beta$1 DNA fragments having the sizes expected for the free pSVEIF plasmid DNA (FIG. 1), indicating that the human IFN-1 gene is integrated in the CHO genome as part of concatemers of pSVEIF DNA molecules. The additional fragments, different for each clone, probably represents the flanks of the integration site; the number and intensity of these bands suggested in most cases a single integration site. In most pSVEIF-CHO clones, the amount of IFN-$\beta$1 DNA per cell was of the same order of magnitude as in human cells and varied without relation to IFN production.

The poly A+RNA of one clone, pSVEIF-1, was analyzed by agarose gel electrophoresis, blotting to nitrocellulose and hybridization to IFN-$\beta$1 DNA. Two IFN-$\beta$1 RNAs, of 1150 and 2200 bases respectively, were seen corresponding to the two possible polyadenylation sites in the pSVEIF-DNA (FIG. 1), one in the IFN-$\beta$1 gene (near the HincII-HindIII boundary) and one in the SV40 early gene (between Bc11 and BamH1, FIG. 1). The two IFN-$\beta$1 RNA species were easily detected in total (nonoligo dT selected) cell RNA of the pSVEIF-1 clone.

pSVEIF DNA was also transfected into monkey COS-7 cells (Gluzman, 1981) which allow the replication of the SV40 recombinant genome. IFN-$\beta$1 activity was detected in the medium of the transfected COS-7 cultures from 48 to 72 hours after DNA addition. The maximum yields were 850 units/1/10^6 cells and much lower than in the pSVEIFCHO cells. Controls showed that this is probably not due to an effect of IFN on SV40 replication, but rather to autoinhibition of the SV40 early promoter by Tantigen (Hansen et al, 1981). The pSVEIF DNA was also co-transfected into mouse L TK-cells (Wigler et al, 1979) with pAGO DNA (Colbere-Garrapin et al, 1981). Some clones produced up to 1500 units IFN/ml; addition of poly (rI)(rC) or of cycloheximide, with DEAE-dextran (Maroteaux et al, 1983b) did not stimulate human IFN production by these pSVEIF-mouse L cells, while mouse IFN was inducible in the same cells (not shown).

Role of the Promoter Sequences in Constitutive and Inductible Expression of the IFN-$\beta$1 Gene To varify the role of the SV40 promoter in constitutive expression, we studied the expression of the unmodified human IFN-$\beta$1 gene in CHO transformed cells. CHO-K1 DHFR-cells were transfected by the 1.83 kb EcoR1 genomic fragment containing the IFN-$\beta$1 gene with 300 bp of 5'-flanking DNA (Ohno and Taniguchi 1981) ligated to EcoR1-cut pSVDHFR-DNA. In such transformed clones (pDIF series), human IFN activity was found only after poly (rI)(rC) superinduction, but no constitutive production was seen as in pSVEIF-CHO clones (Table 2). However, the level of expression of the unmodified human IFN-$\beta$1 gene in superinduced CHO cells was very low (128 U/ml) as compared to the pSVEIF constitutive expression.

High levels of inducible expression were obtained in CHO cells when the IFN-$\beta$1 gene was fused to the promoter of another poly (rI)(rC)-inducible human gene, IFN-$\beta$2 (Weissenbach et al, 1980; Maroteaux et al, 1983a). In this construction (p$\beta$2pro-$\beta$1), the 5' untranslated region of the IFN-$\beta$1 gene (from the Taq1 site, 20 bp after the RNA start) is fused to the XhoI site located 10 bp downstream from the

TABLE 2
INDUCIBLE IFN EXPRESSION WITH IFN-β1 and β2 PROMOTERS

| Induction Conditions | FN Activity Units/ml | | |
|---|---|---|---|
|  | pβ2pro-β1* | pDIF** | CHO+*** |
| Non induced | 64 | <1 | <1 |
| polyI:C | 272 | 16 | 4 |
| polyI:C + CH + ActD | 1375 | 128 | 12 |
| CH + ActD | 1250 | 48 | ND |
| NDV | 312 | 154 | 6 |
| Sendai virus | 875 | ND | ND |

*CHO clone transformed by IFN-β1 gene fused to IFN-B2 promoter
**CHO clone transformed by IFN-β1 with its own promoter
***CHO clone without human IFN gene. Confluent cultures in 9 cm plates were induced as in Weissenbach et al (1980) for 4 hours with 100 μg/ml poly (rI)(rC), and/or 50 g/ml cycloheximide (CH) with 1 μg/ml Actinomycin D for the last 30 minutes. Cells were washed three times and 5 ml medium were added. IFN activity was assayed in the medium after 18 hours. Induction with Sendai or Newcastle disease virus (NDV) was as in Maroteaux et al (1983b) and Mitrani-Rosenbaum et al (1983).

B2 promoter's RNA start site (FIGS. 2 and 4). CHO-K1 DHFR-cells were transformed by pβ2pro-β1 DNA ligated (after EcoR1) to pSVDHFR-DNA, and transformant clones were tested for human IFN-β production. IFN activity was found only if the cells were induced by poly (rI)(rC), superinduced by cycloheximide and actinomycin D, or virusinfected (Table 2). As found for the IFN-β2-mRNA in human cells (Weissenbach et al, 1980, induction of the pβ2pro-β1 CHO cells was also observed with cycloheximide and actinomycin D treatment without poly (rI)(rC). The β2 promoter was much stronger than the β1 promoter in the CHO cells, and demonstrates that the promoter region determines the inductivility of the gene.

It should be noted that in both pSVEIF and pβ2pro-β1 constructions, the promoter segment used also contained a part of the 5'-end of the mRNA sequence (FIG. 2). For this reason, it is possible that not only transcriptional but also post-transcriptional regulations could contribute to the differential expression of the IFN-β1 gene in CHO cells transformed by pSVEIF and pβ2pro-β1 DNAs. This could explain the effect of cycloheximide which seem to act on the stability of the mRNA (Cavalieri et al, 1977; Raj and Pitha, 1983; Maroteaux et al, 1983b).

Amplification of the IFN-β1 Gene in pSVEIF-CHO Cells

Clones of pSVEIF-CHO cells were selected for resistance to 50 nM and 1 μM methotrexate. Resistant clones (MEIF-5 series) derived from pSVEIF-5 cells (Table 1) showed a 10 to 20 fold increase in their constitutive production of IFN activity, the highest titers being 350,000 U/ml. Further selection of MEIF-5-1 cells which have been designated as cell line CHO-β1-5-9 and deposited at the Pasteur Institute under Accession No. I-340, for resistance to 300 nM methotrexate improved IFN-β1 yields to $10^6$ units per day/$10^6$ cells. Southern blot analysis of the MEIF-5-1 clone DNA showed a 15 fold amplification of the IFN-β1 sequences integrated in these cells. However, methotrexate-resistant clones derived from another pSVEIF-CHO clone, showed no amplification of IFN production (Table 1). Differences in the chromosomal location of the IFN-β1 gene and in its proximity to the amplifiable pSVDHFR DNA, probably account for the different behaviour of the two cell lines.

Constitutive production of IFN was studied in more detail in cultures of MEIF-5-1 CHO cells. Confluent cultures of these cells produce, in the steadystate, about 200,000 Units/day/$10^6$ cells (Table 1). After change of the culture medium, a linear accumulation of IFN can be observed for 16-18 hours after which a plateau level is slowly reached (FIG. 3). This plateau could result from either breakdown of IFN or from some inhibition of IFN synthesis. Change of the culture medium every 24 hours, produced new rounds of IFN accumulation (Table 3). After medium change, the rate of IFN-β1 accumulation (FIG. 3) was approximately 5,000 Units/hour/$10^6$ cells, or 300,000 IFN-β1 molecules per cell and per hour.

The growth-rate of the MEIF-CHO cells appears 30-40% lower than that of CHO+ cells transformed only by the pSVDHFR DNA (Table 3). This difference could be explained by an inhibitory effect of the large amounts of human IFN-β produced on the growth of the hamster cells. Human IFN-β seems to cross-react to some extent with hamster cells as shown by the 30% growth inhibition and by the increase in (2'-5') oligo A sythetase produced by 100 U/ml of pure human IFN-β in CHO+ cells (Table 3). A lower concentration of 200 U/ml, which fully induces the enzyme in human cells, gave only a small increase in CHO+ cells.

TABLE 3
Human IFN production and Growth of MEIF-CHO cells

|  | Cell cultures: | | | |
|---|---|---|---|---|
|  | Day 2 | Day 3 | Day 4 | Day 5 |
|  | Total IFN recovered, Units/10 6 cells | | | |
| MEIF-5, medium changed daily | 25,000 (—) | 90,000 (65,000) | 200,000 (110,000) | 350,000 (150,000) |
| MEIF-5, medium not changed | 49,000 (—) | 65,000 (16,000) | 71,000 (6,000) | 71,000 (0) |

|  | Cell number, (in million cells) | | (2'-5')oligo A synthetase, cpm |
|---|---|---|---|
| MEIF-5 | 0.69 | 1.24  2.4 | 10,300 |
| CHO+ | 0.95 | 1.7  3.6 | 170 |
| CHO+ with HuIFN-B* | 0.7 | 1.5  2.5 | 6,250 |

*1000 units/ml human IFN-β added at day 2.
The total amount of IFN recovered calculated per 10 6 cells is given. Number in parenthesis indicate the daily increment in IFN. Cells were counted in a Coulter counter. The (2'-5') oligo-A synthetase was measured on day 3.

MEIF-CHO cells have a high (2'-5') oligo A synthetase level as compared to untreated CHO+ cells, indicating that they respond to the human INF-β1 that they produce (Table 3). The slow growth could be related to this autostimulation of the (2'-5') oligo A synthetase (Kimchi et al, 1981), but could also result from additional disorders due to amplification of the DHFR gene in these cells.

Large-Scale Production and Purification of IFN-β1 from MEIF-CHO Cultures

The MEIF-5-1 cells were grown for several weeks, with daily change of the culture medium, in Roller bottles containing 150-200×$10^6$ cells. Yields of IFN were 20-40×$10^6$ units (40-80 μg) per bottle and per day. The collected media were subjected to chromatography on Cibacron Blue Sepharose (Knight and Fahey, 1980) from which the IFN-β1 was eluted with 40% propylene glycol. This material was loaded on a column of monoclonal antibodies (117-1), which had been prepared against IFN-β from human fibroblasts (Novick et al, 1983). In the experiment of table 4, about 2×$10^8$ units of MEIF-CHO material was purified on the monoclonal antibodies column (4 ml; 28 mg IgG) and eluted by Na citrate-HCl pH 2. The specific activity of the eluted material was 4.9×10⁸ units per mg protein, very close to the specific activity of pure human IFN-β(5×10⁸ units/mg) (Novick et al, 1983). Electrophoresis on polyacrylamide gels shows a band at 22,000-Mr, which migrates identically to IFN-β purified from human diploid fibroblast cultures. Uncleaved pre-IFNβ1 would be 20,000-Mr and unglycosylated 18,000-Mr (Knight and Fahey, 1982). The IFN-β1 produced by the MEIF-CHO cells is, therefore, identical in its immunological and size characteristics, to the native human IFN-β1.

TABLE 4

Immunoaffinity purification of Hu IFN- 1 from MEIF-CHO cells

| Sample | Volume (ml) | IFN activity (million units) | Protein (mg) | Specific activity (units/mg protein) | Yield (%) |
| --- | --- | --- | --- | --- | --- |
| Blue-Sepharose eluate (40% propyleneglycol) | 70 | 280 | 36.7 | $7.6 \times 10^6$ | 100 |
| Loaded on McAb column after ultrafiltration | 20 | 220 | 12.6 | $1.75 \times 10^7$ | 79 |
| Unbound McAb eluate citrate pH2 | 25 | 6.3 | | | |
| #1 | 5 | 20 | 0.065 | $3.0 \times 10^8$ | |
| #2 | 5 | 200 | 0.41 | $4.9 \times 10^8$ | 82 |
| #3 | 5 | 10 | 0.05 | $2.0 \times 10^8$ | |

Monoclonal antibodies 117-1 IgG (28 mg) on 4 ml agarose.

A 24 ml column of 117-1 IgG-agarose was used repeatedly to purify up to 8×10⁹ units IFN-β1 (16 mg) from MEIF-5 cells, with a yield of 80–100%. Comparison of the material loaded on the column with the effluent, shows the near complete removal of the 22,000-MR protein from the contaminating proteins originating mainly from the serum used for the cell cultures (FIG. 6). In the eluted IFN-β, no contaminants which might have leaked from the antibody column, were seen.

DISCUSSION

A main goal of recombinant DNA technology is to produce large amounts of valuable proteins in a form that should be identical to the natural product. In the case of the human IFN-β1glycoprotein, direct expression of the DNA sequence coding for the processed mature IFN-β1 in *E. coli* yields an unglycosylated analog (Derynck et al, 1980). In addition, the IFN-β1produced by *E. coli* seems to be unstable and, upon purification by immunoaffinity chromatography, turns out to contain up to 90% of inactive IFN-β1 protein (unpublished results). This may result from abnormal disulfide bridge formation in the bacteria (D. Marks, private communication). We show here that expression of the DNA coding coding for pre-IFN-β1 in hamster cells leads to the secretion of a protein which is electrophoretically identical to the natural glycoprotein and which gives, upon purification by immunoaffinity on monoclonal antibodies, the same specific activity as the IFN-β1 purified from human fibroblasts. Hamster cells glycosylate proteins identically to human cells (Kornfeld and Kornfeld, 1980). Further advantages of the present MEIF-CHO cell system are the constitutive expression and gene amplification. To produce the natural IFN-β1, mass cultures of human fibroblasts have to be superinduced by a combined treatment of poly (rI) (rC), cycloheximide and actinomycin D (Havell and Vilcek, 1972). In our routine experience, human foreskin cells produce around 20,000 units IFN-β per ml and per 10⁶ cells, in each round of superinduction. The cells do not survive long after induction and new cultures have to be grown. The MEIF-CHO cells, described here, secrete 200,000 units per ml and 10⁶ cells, i.e. 10 times more than superinduced human fibroblasts, and the continuous production allows daily harvests. If the culture medium is replaced every day, the cultures can be maintained for months. Human IFN-β1 secretion does not deteriorate the hamster cells, although a growth-inhibitory effect and an increase in (2'–5') oligo A synthetase are seen probably as a result of some cross-activity of the human IFN-β1 on the hamster IFN receptors. In practical terms, the production of IFN-β1 per month and culture vessel (e.g. roller bottle) can be 100 times that of human fibroblasts. It is also higher than what we obtained in mouse cells (Malpiece et al, 1983). Combination with the efficient purification scheme described here, makes the MEIF-CHO cell cultures a convenient procedure to obtain large amounts of pure human IFN-β1.

Similar methods have been described for the constitutive expression of human IFN-α5 and IFN-γ cDNA (Haynes and Weissmann, 1983; Scahill et al, 1983) in CHO cells, with yields of 20–100,000 U/ml and per day for IFN-α5 and of 50,000 U/ml for IFN-γ. We have, recently, introduced a 5.6 kb genomic fragment containing the human IFN-γ gene (Gray et al, 1982) in the pSVE3 vector. CHO clones producing continuously 150,000 U/ml of IFN-γ were obtained, indicating that large intron-containing genes can be efficiently expressed by this system (Mory et al, in preparation). In the present work with the intron-less IFN-β1 gene, we did not introduce splicing junctions in the pSVEIF DNA construction as done for IFN-α5 (Hayes and Weissman, 1983). Moreover, the selectable pSVDHFR DNA and the pSVEIF DNA were not ligated before transfection into CHO cells. The transformation efficiency was not reduced, but several clones did not amplify the IFN-β1 gene nor increase IFN production when selected for methotrexate resistance, possibly because the DHFR gene could be amplified without necessarily causing amplification of the IFN gene.

In this work, we also verified that the constitutive expression of the IFN-β1 gene is a function of the promoter used, and not a property of the transformed CHO cells. When IFN-β1 DNA was fused to the poly (rI)(rC)-inducible IFN-β2 promoter before its transfer into CHO cells, no IFN production was seen unless the cells were induced by poly (rI)(rC) or by cycloheximide/Actinomycin D. Similarly, Weidle and Weissmann (1983) showed that an IFN promoter makes the expression of globin DNA sequences, inducible by virus infection. Several sequences seem to be playing a role in the inducible expression of the IFN genes (Ragg and Weissmann, 1983; Dinter et al, 1983; Maroteaux et al, 1983; Tavernier et al, 1983; Zinn et al, 1983) but the mechanisms involved (transcriptional or post-transcriptional) are not yet known. What seems clear is that when the IFN-$\beta$1 DNA is fused to the SV40 early promoter, induction by poly (rI)(rC) and cycloheximide has no more effect and constitutive production is observed. An important goal would be now to improve the constitutive expression to make IFN-$\beta$1, which is poorly expressed in human cells, a major product of the recombined cell.

Industrial Production of Human IFN-$\beta$1 from MEIF-5 CHO Cells

To obtain maximal yields of human IFN-$\beta$1, the preferred embodiment of the present invention is to grow the MEIF-5 CHO cells to high density on suitable glass, plastic or other polymeric surfaces (e.g. roller bottles, microcarrier beads) and maintain the cultures with daily change of medium. The culture medium (Dulbecco's modified minimal essential medium from GIBCO Ltd, with 150 $\mu$g/ml L-proline) should contain a minimal amount of foreign proteins. We have found that 1% fetal calf serum in the medium is sufficient to give optimal IFN yields. As an example, a group of 50 roller bottles (empty volume 1.5 liters per bottle) containing a total of $10^{10}$ cells attached to the walls of the bottles, and a total of 10 liters culture medium, was maintained continuously for 4 months in a Roller apparatus (Bellco) at 37° C. Each day, an average of $1.5 \times 10^9$ units IFN-$\beta$1 (3 mgs) were collected, giving a total of $1.8 \times 10^{11}$ units IFN-$\beta$1 (360 mgs) in 4 months. Considering that the usual therapeutic dose of IFN is $3 \times 10^6$ units, this represents 60,000 doses of the drug. This is 100 times more than what could be produced in a comparable production unit of 50 roller bottles, using human diploid fibroblasts which require superinduction by poly (rI)(rC), cycloheximide and actinomycin D. The procedure resulting from the present invention also eliminates the multiple manipulations needed for the induction of human cells, and cuts down the production costs in manpower and material by a factor of 50.

The MEIF-5 CHO cells can also be grown on microcarrier beads, for example cytodex III (Pharmacia Fine Chem.), which can be then maintained in industrial fermentors with adequate controls of temperature, pH, dissolved carbon dioxide and oxygen. The IFN-$\beta$1 secreted into the medium can then be recovered by a continuous flow process.

The IFN-$\beta$1 in the collected culture medium was stored at 4° C. and Blue Sepharose (Pharmacia Fine Chem.) was added to the solution, with stirring for 16 hours. The Blue Sepharose beads were collected by filtration, washed with KCl 1.5M, and the IFN-$\beta$1 activity was eluted by a 40% propylene glycol solution. Ultrafiltration under mild pressure through a YM10 Amicon membrane was used to concentrate 4 fold the protein solution and reduce the propylene glycol concentration to 10%. The IFN-$\beta$1 can be purified to homogeneity from this solution by affinity chromatography on the above described monoclonal antibody column prepared by binding 7 mgs IgG 117-1 per ml of agarose-polyacryl hydrazide. A 250 ml column can purify 150 mg of IFN-$\beta$1, which is eluted by 50 mM citric acid-HCl pH 2 with a recovery of 80%. The eluted material is homogenous, titers over $100 \times 10^6$ units/ml and $5 \times 10^8$ units/mg protein, as illustrated above. To improve stability and shelf-life of the so-produced IFN-$\beta$1, the solution can be dialyzed against acetate buffer pH 3.5, and supplemented by human serum albumin fraction V, mannitol, polyvinyl pyrrolidone (1,000 to 50,000 Mr), and lyophilized in vacuo with constant temperature control. Such preparations are stable for 1 year at 4° C.

In a preferred embodiment of the invention the composition is supplemented with human serum albumin Fraction V about 40 mgs, mannitol about 10 mgs., polyvinyl pyrrolidone (1,000 to 50,000 Mr) 40 mgs., for $0.1-10 \times 10^6$ units of IFN-$\beta$1.

MATERIALS AND METHODS

Recombinant plasmid DNAs

Transformation of *E. coli* MM294 (Backman et al, 1976), preparation of plasmid DNA and cutting by restriction enzymes, separation of DNA fragments by agarose-gel electrophoresis and DNA ligation were carried out by standard procedures as described in Maniatis et al (1982).

SV40 early promoter-IFN $\beta$1 fusions: pSVEIF-DNA

An 1.83 kb EcoR1 fragment of human genomic DNA containing the IFN-$\beta$1 gene, was derived from the previously described lambda charon 4A clone C15 (Mory et al, 1981), ligated to EcoR1-cut pBR322 DNA and cloned in *E. coli* MM294 (clone 631, FIG. 1). The pSVE3 vector, containing the SV40 origin of replication and early gene region, was described by Hartman et al (1982). pSVE3 is composed of the 2.845 kb HpaII-BamH1 fragment of SV40 strain 776 DNA, spanning coordinates 346 to 0/5235 to 2533 (Tooze, 1980), which was cloned after adding BamH1 linkers to the HpaII end, within the BamH1 site of the pBRM plasmid. pBRM is a fragment of pBR322 from the HaeII site at position 2352 through the ampicillin resistance gene to EcoR1 (4362), resealed with the use of BamH1 linkers which also restored the EcoR1 site (Hartman et al, 1982). pSVE3 was cut with HindIII, removing the 5107-3412 sequences of SV40 DNA, and was dephosphorylated by calf thymus alkaline phosphatase (Boehringer), before ligation with T4 DNA ligase (Boehringer) to a 0.77 kb HincII fragment of IFN-$\beta$1 DNA to which HindIII linkers were added. Clones in which the INF-$\beta$1 coding sequence is oriented as the SV40 early promoter were selected (pSVEIF, Fig. 1).

Plasmid pSVDHFR contains the mouse dihydrofolate reductase cDNA following the SV40 early promoter HindIII site and a splicing region of mouse IgG-$\gamma$2a (FIG. 1) (M. Horowitz and P. Sharp, personal communication). This plasmid was provided by Dr. M. Horowitz.

Fusion of INF-$\beta$1 to the INF-$\beta$2 promoter: p$\beta$2pro-$\beta$1 DNA

The cDNA clone A341 (INF-$\beta$2) described previously by Weissenbach et al (1980), and which corresponds to a poly (rI)(rC)-induced 14S mRNA yielding antiviral activity upon translation in xenopus oocytes, was used to isolate the genomic DNA clone IFA-2 (FIG. 5) from our partial EcoR1 human genomic bank in lambda charon 4A (Mory et al, 1981). The promoter region of the IFA-2 Gene has been sequenced (Maroteaux et al, 1981a) and was excised as a 2.6 kb XhoI fragment from IFA-2 phage DNA. XhoI cuts 20 bp after the RNA start site (FIG. 2). After forming blunt ends by filling in with DNA polymerase I, HindIII linkers were attached to the 2.6 kb XhoI fragment which was recut with EcoR1, and cloned in EcoR1, HindIII- cut pBR322. The plasmid DNA was cut with HindIII, dephosphorylated and ligated to a 0.83 kb TaqI fragment of INF-$\beta$1 DNA (clone 631), to which HindIII linkers had been attached. TaqIcuts in the INF-$\beta$1 gene at 20 bp after the RNA start and 20 bp after the poly (A) addition site. A clone in which INF-$\beta$1 was oriented as the INF-$\beta$2 promoter was chosen (p$\beta$2 pro$\beta$1, FIG. 5).

Cell Transformations and DNA, RNA Analysis

A DHFR-deficient mutant of hamster CHO-K1 cells (clone DXB11) was obtained from Dr. L. Chasin (Urlaub and Chasin, 1980). Cells were grown in MEM medium (F12, Gibco) with 10% fetal calf serum (FCS) at 37 C in 8% or 5% $CO_2$. For DNA transfections, $5 \times 10^5$ cells were cultured for one day in a 9 cm plate before adding a $CaPO_4$-DNA coprecipitate, which was prepared (Busslinger et al, 1981) by mixing 10 mg DNA dissolved in 0.45 ml of Tris-Hcl pH 7.9, 0.1 mM EDTA with 0.5 ml of 280 mM NaCl, 1.5 mM $Na_2HPO_4$, 50 mM Hepes buffer pH 7.1, before adding 0.05 ml of 2.5M $CaCl_2$ with gentle shaking and letting precipitate for 30–40 minutes. For the pSVEIF-CHO clones, the DNA was a mixture of 2 $\mu$g pSVDHFR plasmid DNA with 4.5 $\mu$g pSVEIF DNA (molar ratio of 1 to 5 respectively). The pDIF-CHO clones were obtained by transfection with pSVDHFR DNA, cut by EcoR1 and ligated to a 5 fold molar excess of the 1.83 kb EcoR1 IFN-$\beta$1 genomic fragment of clone 631 DNA. For the p$\beta$2pro-$\beta$1 -CHO clones, transfection was with EcoR1-cut pSVDHFR DNA ligated to a 5 fold molar excess of EcoR1-cut p$\beta$2pro-$\beta$1 DNA.

After adding the $CaPO_4$-DNA, the cells were left at room temperature for 30 minutes, 9 ml of F-12 or MEM-10% FCS were added and the cultures returned to the $CO_2$ incubator for 4 hours. Medium was removed and the cells were osmotically shocked with 10% glycerol in F-12 or MEM for 4 minutes. Cells were washed and incubated 48 hours in F-12 or MEM-10% FCS. The cells were then trypsinized and subcultured 1:4 into selective medium (Urlaub and Chasin, 1980) composed of DMEM (H21, Gibco), 150 $\mu$g/mLproline and 10% FCS which had been extensively dialyzed against phosphate-buffered saline. In some cases, MEM alpha medium without nucleosides (F20, Gibco) was used. Medium was changed every 3-4 days, and clones were isolated after 10–12 days, trypsinized in cylinders and grown to mass cultures.

RNA was purified from NP-40 cytoplasmic extracts as before (Weissenbach et al, 1979), electrophoresed and analyzed by NOrthern blot hybridization as detailed (Fellows, et al, 1982). Total cellular DNA was extracted as in Wigler et al (1979) and used for Southern blot hybridization (Southern, IFN Assays and Purification Assay of human IFN was carried out in the medium of confluent cultures, by measuring the reduction in the cytopathic effect of Vesicular Stomatitis Virus (VSV) in human diploid foreskin cells FS11 or on WISH cells, according to established procedures (Novick et al, 1983). The assay was calibrated against the IFN-$\beta$ reference standard G-023-901-527 of NIH. For affinity chromatography (Novick et al, 1983), the MEIF-CHO IFN purified on Blue-Sepharose (Pharmacia) and eluted by 1M NaCl, 40% propylene glycol (PG), 20 mM phosphate buffer pH 7, was concentrated by ultrafiltration on a YM10 membrane (Amicon). The concentrated IFN solution in 0.15M NaCl, 15 mM phosphate buffer pH 7 (PBS) with 10% PG, was loaded on the monoclonal anti-IFN antibody column prepared binding 7 mg IgG from hybridoma 118-1 per ml of agarose-polyacryl hydrazide (Wilcheck and Miron, 1974). The column was washed at 4° C., with a flow-rate of 0.5 ml/minute, with 25 volumes PBS, and IFN was eluted by cold 50 mM citric acid-HCl pH 2. Fractions of one column volume were collected in 25% PG and kept at 4 C. For gel electrophoresis, samples were boiled 5 minutes with 2% B-mercaptoethanol, 3% Sodium dodecyl sulfate (SDS), run on a 15% polyacrylamide slab gel in SDS and visualized by coomassie blue or by silver stain (Sammons et al, 1981).

REFERENCES

Alt, F. W., Kellems, R. E., Bertino, J. R. and Schimke, R. T. (1978) J. Biol. Chem. 253, 1357–1370.

Backman, K., Ptashne, M. and Gilbert, W. (1976) Proc. Nat'l. Sci. USA, 73, 4174–4178.

Burke, D. C. (1980) in Gresser, I. (ed.), Interferon 2, Acad. Press, New York, pp. 47–64.

Busslinger, M., Moschonas, N. and Flavell, R. (1981) Cell 27, 289–298.

Camaani, D. and Berg, P. (1982) Proc. Natl. Acad. Sci. USA, 79, 5166–5170.

Cavalieri, R. L., Havell, E. A., Vilcke, J. and Petske, S. (1977) Proc. Natl. Acad. Sci. USA, 74, 4415–4419.

Colbere-Garapin, F., Horodniceanu, F., Kourilsky, P. and Garapin, A. C. (1981) J. Mol. Biol. 150, 1–14.

Degrave, W., Derynck, R., Tavernier, J., Haegeman, B. and Fiers, W. (1981) Gene 14, 137–143.

Derynck, R., Remaut, E., Saman, E., Stanssens, P., De Clercq, Jr., Content, J. and Fiers, W. (1980) Nature 287, 193–197.

Dinter, H., Hauser, H., Mayr, U., Lammers, R., Bruns, W., Gross, G. and Collins, Jr. (1983) in DeMaeyer, E. and Schellekens, H. (eds.) The Biology of the Interferon System, Elsevier Science Publ., Amsterdam, in press.

Fellows, M., Nir, U., Wallach, D., Merlin, G., Rubinstein, M. and Revel, M. (1982) Proc. Natl. Acad. Sci. USA, 79, 3082–3086.

Gluzman, Y. (1981) Cell 23, 175–182.

Graham, F. and Van der Eb, A. (1973) Virology 52, 456–457.

Gray, P. W. and Goeddel, D. V. (1982) Nature 298, 859–863.

Gross, B., Mayr, U., Bruns, W., Grosveld, F., Dahl, M. H. M. and Collins, J. (1981) Nucleic Acids Res., 9, 2495–2507.

Hansen, U., Tenen, D. J., Livingston, D. M. and Sharp, P. (1981) Cell 27, 603–612.

Hartman, J. R., Nayak, D. P. and Fareed, G. C. (1982 Proc. Natl. Acad. Sci. USA, 79, 233–237.

Hauser, H., Gross, B., Bruns, W., Hochkeppel, H. K., Mayr, U. and Collins, J. (1982) Nature 297, 650–654.

Havell, E. A. and Vilcek, J. (1972) Antimicrob. Agents Chemother. 2, 476,484.

Haynes, J. and Weissman, C. (1983) Nucleic Acids Res., 11, 687–706.

Kaufman, R. J. and Sharp, P. A. (1982) J. Mol Biol. 159, 601–621.

Kimchi, A., Shure, H. and Revel, M. (1982) Eur. J. Biochem. 114, 5–10.

Knight, E. and Fahey, D. (1981) J. Biol. Chem. 256, 3609–3611.

Knight, E. and Fahey, D. (1982) J. Interferon Res., 2, 421–429.

Kornfeld, R. and Kornfeld, S. (1980) in Lennarz, W. J. (ed.), The Biochemistry of Glycoprotein and Proteoglycans; Plenum Press, pp. 1–83.

Lawn, R. M., Adelman, J., Franke, A. E., Houck, C. M., Gross, M., Najarian, R. and Goeddel, D. V. (1981) Nucleic Acids Res., 9, 1045–1053.

Malpiece, Y., Michel, M. L., Carloni, G., Revel, M., Tiollais, P. and Weissenbach, J. (1983) Nucleic Acids Res., 11, 4645–4654.

Maniatis, T., Fritsch, E. F. and Sambrook, J. (1982) Molecular Cloning, published by Cold Spring Harbor Laboratory Press, N.Y.

Maroteaux, L., Kahana, C., Mory, Y., Groner, Y. and Revel, M. (1983a) EMBO J. 2, 325–332.

Maroteaux, L., Chen, L., Mitrani-Rosenbaum, S., Howley, P. M. and Revel, M. (1983b) J. Virol. 47, 89–95.

Mitrani-Rosenbaum, S., Maroteaux, L., Mory, Y., Revel, M. and Howley, P. M. (1983) Mol. Cell. Biol. 3, 233–240.

Mory, Y., Chernajovsky, Y., Feinstein, S. I., Chen, L., Nir, U., Weissenbach, J., Ohno, S. and Taniguchi, T. (1981) Proc. Natl. Acad. Sci. USA, 78, 5305–5309.

Ohno, S. and Taniguchi, T. (1982) Nucleic Acids Res., 10, 967–977.

Ragg, H. and Weissman, C. (1983) Nature 303, 439–442.

Raj, N. B. K. and Pitha, P. M. (1981) Proc. Natl. Acad. Sci. USA, 78, 7426–7430.

Raj, N. B. K. and Pitha, P. M. (1983) Proc. Natl. Acad. Sci. USA, 80, 3923–3927.

Ringold, G., Dieckmann, B. and Lee, F. (1981) J. Mol. App. Genetics, 1, 165–175.

Sammons, D. W., Adams, L. D. and Mishizawa, E. E. (1981) Electrophoresis 2, 135–141.

Scahill, S. J., Devos, R., Van der Hayden, J. and Fiers, W. (1983) Proc. Natl. Acad. Sci. USA, 80, 4654–4658.

Sehgal, P. B., Lyles, D. S. and Tamm, I. (1978) Virology 89, 186–198.

Southern, E. M. (1975) J. Mol. Biol. 98, 503–517.

Tan, Y. H., Armstrong, J. A., Ke, Y. H. and Ho, M. (1970) Proc. Natl. Acad. Sci. USA, 67, 464–471.

Tavernier, J., Gheysen, D., Duerinck, F., Van der Hayden, J. and Fiers, W. (1983) Nature 301, 634–636.

Tooze, J. ed. (1980) DNA tumor virus, published by Cold Spring Laboratory Press, N.Y.

Urlaub, G. and Chasin, L. A. (1980) Proc. Natl. Acad. Sci. USA 77, 4216–4220.

Weidle, U. and Weissman C. (1983) Nature 303, 442–446.

Weissenbach, J., Zeevi, M., Landau, T. and Revel, M. (1979) Eur. J. Biochem. 98, 1–8.

Weissenbach, J., Chernajovsky, Y., Zeevi, M., Shulman, L., Soreq, H., Nir, U., Wallach, D., Perricaudet, M., Tiollais, P. and Revel, M. (1980) Proc. Natl. Acad. Sci. USA, 77, 7152–7156.

Wigler, M., Sweet, R., Sim, G. K., Wold, B., Pellicer, A., Lacy, E., Maniatis, T., Silverstein, S. and Axel, R. (1979) Cell 16, 777–785.

Wilchek, M. and Miron, T. (1974) Methods Enzymol. 34, 72–76.

Zinn, K., Mellon, P., Ptashne, M. and Maniatis, T. (1982) Proc. Natl. Acad. Sci. USA, 79, 4897–4901.

What is claimed is:

1. A Chinese hamster ovary cell designated CHO-$\beta_1$-5-9 and deposited with the Pasteur Institute under Order No. I-340 which is resistant to >50 nM methotrexate comprising the selectable marker pSVDHFR and a pSVEIF DNA molecule which contains a sequence encoding human fibroblast interferon IFN-beta 1 fused about 60 base pairs downstream from the SV40 early start gene, the cell being capable of being cultured in a culture medium so as to constitutively express the sequence encoding human fibroblast interferon IFN-beta 1, produce an IFN-beta 1 glycoprotein at yields greater than 50,000 units/$10^6$ cells/24 hours, and secrete the IFN-beta 1 glycoprotein into the culture medium.

2. A method of producing human IFN-$\beta 1$ with cells derived from the cell of claim 1 which comprises growing the cells in a suitable culture medium and on a suitable surface, maintaining the culture at a temperature of about 37° C., periodically replacing the culture medium, collecting the culture medium that has been replaced, contacting the collected medium with an affinity chromatography adsorbent so as to retain the IFN-$\beta 1$ secreted by the cells into the medium, washing the adsorbent containing the IFN-$\beta 1$ with a suitable solution so as to remove the proteins other than IFN-$\beta 1$ that have not been adsorbed, eluting the IFN-$\beta 1$ from the adsorbent with a suitable solution, purifying the eluate containing the IFN-$\beta 1$ by affinity chromatography with monoclonal antibodies prepared against IFN-$\beta 1$ from human fibroblasts and eluting the homogeneous IFN-$\beta 1$ bound to the monoclonal antibodies by washing with a suitable solution.

3. A method as in claim 2, wherein the suitable surface is glass, plastic or other polymeric substances.

4. A method as in claim 2, wherein the suitable surface is microcarrier beads.

5. A method as in claim 2, wherein the culture medium is periodically changed about every 24 hours.

6. A method as in claim 2, wherein the culture medium is subject to a continuous flow process.

7. A method as in claim 2, wherein the eluate containing the IFN-$\beta 1$ is concentrated before purifying by affinity chromatography with monoclonal antibodies.

8. A method as in claim 7, wherein the concentration is by ultrafiltration.

9. A method of producing human IFN-$\beta 1$ with cells derived from the cell CHO-$\beta_1$-5-9, Pasteur Institute I-340, which comprises growing the cells on a suitable surface in Dulbecco's modified minimal essential medium containing about 150 µg/ml -proline and about 1% fetal calf serum, maintaining the culture at a temperature of about 37° C., replacing the medium about every 24 hours, collecting the medium that has been replaced, contacting the collected medium with the absorbent Blue Sepharose ® so as to retain the IFN-$\beta 1$ secreted by the cells into the medium, washing the adsorbent containing the IFN-$\beta 1$ with 1.5M KCl so as to remove proteins other than IFN-$\beta 1$ that have not been adsorbed, eluting the IFN-$\beta 1$ from the absorbent with a 40% propylene glycol solution, concentrating the eluate about 4 fold and reducing the propylene glycol concentration to about 10% by ultrafiltration under mild pressure, purifying the concentrated eluate containing the IFN-$\beta 1$ by affinity chromatography with monoclonal antibodies prepared against IFN-$\beta 1$ from human fibroblasts, the antibodies being bound to agarose-polyacryl hydrazide, eluting the homogeneous IFN-$\beta 1$ bound to the monoclonal antibodies by washing with a 50 mM citric acid-HCl with a pH of about 2.

10. A method as in claim 9, wherein the homogeneous IFN-β1 is dialyzed against an acetate buffer of a pH of about 3.5 and supplemented with a composition comprising human serum albumin fraction V, mannitol and polyvinyl pyrrolidone (1,000 to 50,000 Mr).

11. The plasmid designated pSVEIF and deposited with the Pasteur Institut in the host cell line designated CHO-β1-5-9 under Order No. I-340.

* * * * *

UNITED STATES PATENT AND TRADEMARK OFFICE
Certificate

Patent No. 4,808,523                                                    Patented: February 28, 1989

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Michel Revel, Rehovot, Israel; Menachem Rubinstein, Givat Shmuel, Israel; Daniela Novick, Rehovot, Israel; and Yuri Chernajovsky, London, Great Britain.

Signed and Sealed this Sixteenth Day of July 2002.

REMY YUCEL, Ph. D.
*Supervisory Patent Examiner*
Art Unit 1636